United States Patent
Patangay et al.

(10) Patent No.: US 9,713,432 B2
(45) Date of Patent: Jul. 25, 2017

(54) WIDE QRS DETECTOR

(75) Inventors: Abhilash Patangay, Inver Grove Heights, MN (US); Shibaji Shome, Arden Hills, MN (US); Pramodsingh Hirasingh Thakur, White Bear Lake, MN (US); Dan Li, Shoreview, MN (US); Stevens L. Martin, Edina, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1413 days.

(21) Appl. No.: 13/472,563

(22) Filed: May 16, 2012

(65) Prior Publication Data

US 2012/0310101 A1  Dec. 6, 2012

Related U.S. Application Data (60) Provisional application No. 61/491,459, filed on May 31, 2011.

(51) Int. Cl.
| | |
|---|---|
| *A61B 5/0472* | (2006.01) |
| *A61B 5/0452* | (2006.01) |
| A61B 5/00 | (2006.01) |
| A61N 1/362 | (2006.01) |
| A61N 1/365 | (2006.01) |
| A61N 1/37 | (2006.01) |

(52) U.S. Cl.
CPC .......... *A61B 5/0472* (2013.01); *A61B 5/0452* (2013.01); *A61B 5/0031* (2013.01); *A61B 5/7239* (2013.01); *A61N 1/3627* (2013.01); *A61N 1/36507* (2013.01); *A61N 1/37* (2013.01)

(58) Field of Classification Search
CPC ... A61B 5/0031; A61B 5/0472; A61B 5/7239; A61B 5/0452; A61N 1/3627; A61N 1/36507; A61N 1/37
USPC .......................................................... 600/516
See application file for complete search history.

(56) References Cited

U.S. PATENT DOCUMENTS

| | | | |
|---|---|---|---|
| 5,139,027 A * | 8/1992 | Lindecrantz | A61B 5/04525 600/508 |
| 5,527,347 A | 6/1996 | Shelton et al. | |
| 6,370,427 B1 | 4/2002 | Alt et al. | |
| 6,622,040 B2 | 9/2003 | Ding et al. | |

(Continued)

*Primary Examiner* — Edward Moran
*Assistant Examiner* — Pamela M Bays
(74) *Attorney, Agent, or Firm* — Schwegman Lundberg & Woessner, P.A.

(57) ABSTRACT

A system comprises a cardiac signal sensing circuit and a processor circuit. To detect a QRS duration, the processor circuit determines an isoelectric amplitude value of the cardiac signal segment, identifies a time where the cardiac signal segment amplitude deviates from the first isoelectric amplitude value by a specified threshold deviation value as a Q time, determines an isoelectric value time after the determined maxima and minima times that the cardiac signal segment returns to the same or a different isoelectric amplitude value, identifies a time that follows both the determined maxima and minima times and precedes the isoelectric value time as an S time, wherein the cardiac signal segment amplitude at the identified S time satisfies a specified amplitude change criterion from an isoelectric amplitude value, and determines a time duration of the QRS complex in the cardiac signal segment using the identified Q and S times.

20 Claims, 8 Drawing Sheets

(56) References Cited

U.S. PATENT DOCUMENTS

| | | |
|---|---|---|
| 6,766,189 B2 | 7/2004 | Yu et al. |
| 6,804,555 B2 | 10/2004 | Warkentin |
| 6,999,815 B2 | 2/2006 | Ding et al. |
| 7,181,285 B2 | 2/2007 | Lindh et al. |
| 7,283,864 B2 | 10/2007 | Thomas et al. |
| 7,299,086 B2 | 11/2007 | McCabe et al. |
| 7,313,433 B2 | 12/2007 | Yu et al. |
| 7,349,734 B2 | 3/2008 | Stahmann et al. |
| 7,395,216 B2 | 7/2008 | Rosenfeld et al. |
| 7,546,162 B2 | 6/2009 | Ding et al. |
| 2003/0004552 A1* | 1/2003 | Plombon ............... A61N 1/3956 607/27 |
| 2003/0083700 A1* | 5/2003 | Hill ...................... A61N 1/3627 607/9 |
| 2004/0127792 A1 | 7/2004 | Siejko et al. |
| 2004/0243012 A1* | 12/2004 | Ciaccio ............... A61B 5/04011 600/509 |
| 2007/0250125 A1 | 10/2007 | Lindh et al. |
| 2008/0071183 A1 | 3/2008 | Thomas et al. |
| 2008/0097542 A1 | 4/2008 | Yu et al. |
| 2008/0306568 A1* | 12/2008 | Ding .................... A61B 5/0452 607/27 |
| 2008/0319500 A1 | 12/2008 | Zhu et al. |
| 2009/0076404 A1* | 3/2009 | Hopenfeld ........... A61B 5/7239 600/521 |
| 2009/0187227 A1* | 7/2009 | Palreddy .............. A61B 5/0468 607/17 |
| 2009/0281591 A1 | 11/2009 | Shuros et al. |
| 2010/0069987 A1 | 3/2010 | Min et al. |
| 2010/0106209 A1* | 4/2010 | Gunderson .......... A61N 1/3704 607/17 |

\* cited by examiner

WIDE QRS DETECTOR

CLAIM OF PRIORITY

This application claims the benefit of priority under 35 U.S.C. §119(e) of Patangay et al., U.S. Provisional Patent Application Ser. No. 61/491,459, entitled "WIDE QRS DETECTOR", filed on May 31, 2011, which is herein incorporated by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Medical devices also include ambulatory or wearable medical devices (WMDs) such as wearable cardioverter defibrillators (WCDs). WCDs are monitors that include surface electrodes. The surface electrodes are arranged to provide one or both of monitoring surface electrocardiograms (ECGs) and delivering cardioverter and defibrillator shock therapy.

Some medical devices include one or more sensors to monitor different physiologic aspects of the patient. For example, the devices may derive measurements associated with a cardiac depolarization of the patient. Such measurements can provide useful information concerning the cardiac health of the patient.

Methods and systems to identify whether a patient is a responder for cardiac resynchronization therapy by using width of the QRS complex can be found in U.S. Patent Application Publication No. US 2008/0306568, filed Aug. 5, 2008.

Overview

This document relates generally to systems, devices, and methods that provide electrical pacing therapy to the heart of a patient or subject. In particular it relates to, systems, devices, and methods that determine a preferred site of the heart to provide pacing therapy.

A system example includes a cardiac signal sensing circuit to sense a QRS complex in a cardiac signal segment and a processor circuit. The processor circuit includes a peak detector circuit to determine a time of a maxima and a time of a minima in the cardiac signal segment and a QRS complex time duration circuit. The QRS complex time duration circuit determines an isoelectric amplitude value of the cardiac signal segment, identifies a time where the cardiac signal segment amplitude deviates from the first isoelectric amplitude value by a specified threshold deviation value as a Q time in the QRS complex, determines an isoelectric value time after the determined maxima and minima times that the cardiac signal segment returns to the same or a different isoelectric amplitude value, identifies a time that follows both the determined maxima and minima times and precedes the isoelectric value time as an S time in the QRS complex, wherein the cardiac signal segment amplitude at the identified S time satisfies a specified amplitude change criterion from an isoelectric amplitude value, and determines a time duration of the QRS complex in the cardiac signal segment using the identified Q time and S time.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

A medical device (e.g., an IMD or WMD) can include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

Figure 1:
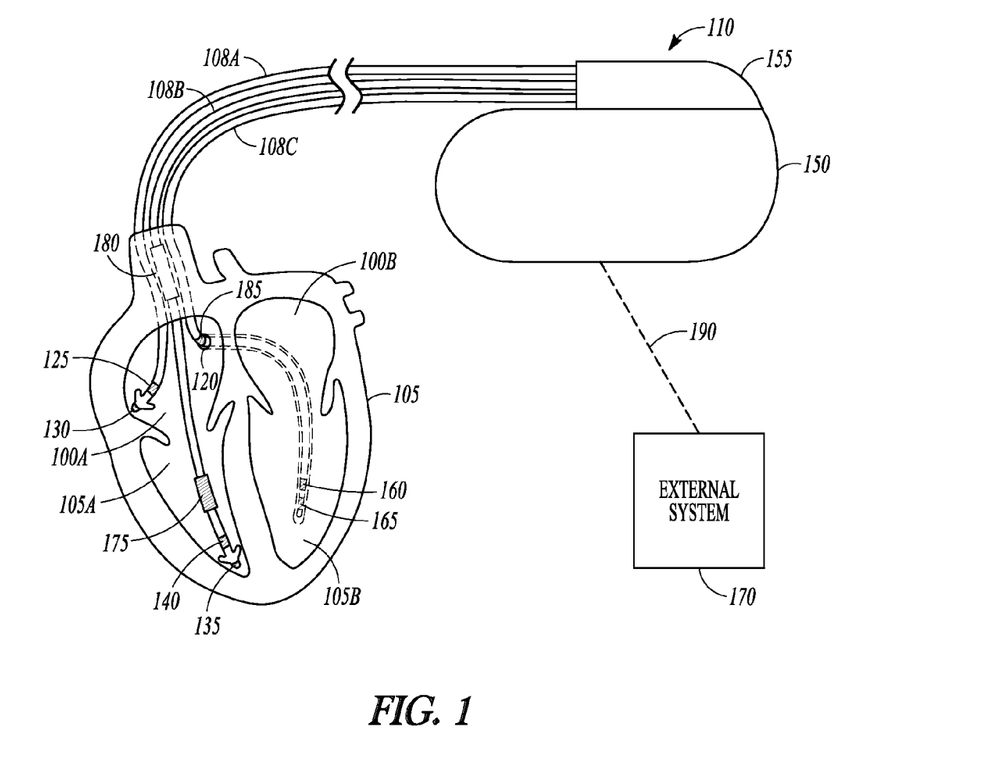
FIG. 1 is an illustration of an example of portions of a system that includes an IMD.

FIG. 1 is an illustration of an example of portions of a system that uses an IMD 110 or other ambulatory medical device that can be capable of moving about with the subject, such as chronically during activities of daily living. Examples of IMD 110 include, without limitation, a pacemaker, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 can be coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Sensed electrical cardiac signals can be sampled to create an electrogram. An electrogram can be analyzed by the IMD and/or can be stored in the IMD and later communicated to an external device where the sampled signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 can include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include anywhere from two to eight electrodes, and may include a ring electrode 185 positioned near the coronary sinus (CS) 120.

Lead 108B can include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. The combination of electrodes used in shock therapy is sometimes called a shock channel or shock vector because the combination of electrodes can result in delivery of therapy in a particular direction. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, an IMD can be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). The present methods and systems will work in a variety of configurations and with a variety of electrodes. Other forms of electrodes include meshes and patches which can be applied to portions of heart 105 or which can be implanted in other areas of the body to help "steer" electrical currents produced by IMD 110.

Figure 2:
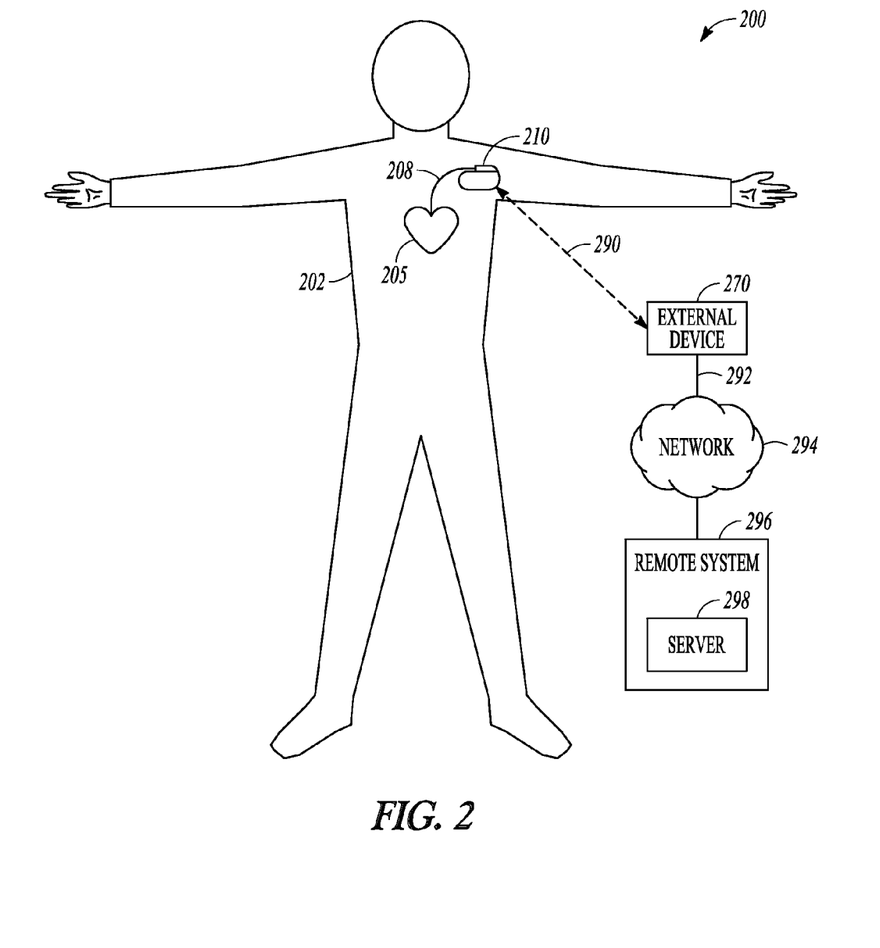
FIG. 2 is an illustration of portions of another system that uses an IMD.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that may be wired or wireless. In some examples, the remote system 296 provides patient management functions and may include one or more servers 298 to perform the functions.

A medical device can monitor electrical activity of the heart of a patient. For example, a WMD may include surface electrodes (e.g., electrodes for skin contact) to sense a cardiac signal such as an electrocardiograph (ECG) of the patient. An IMD may include implantable electrodes to sense a cardiac signal such as an internal electrogram of the patient. Measurements of the cardiac signal can provide useful information concerning the patient's cardiac health.

A sensed cardiac signal can include a QRS complex. The QRS complex is a waveform produced by depolarization of the ventricles and is composed of a Q-wave, an R-wave, and an S-wave. The interval from the onset of the Q-wave to the termination of the S-wave is sometimes called the QRS width or QRS duration. The time duration of the QRS complex can indicate the efficacy of the cardiac contraction. This can be useful to detect proper beat-to-beat capture of the heart by a device that provides pacing stimulation therapy. A shorter QRS complex would indicate proper capture and a longer QRS complex would indicate a less effective contraction.

Changes in the time duration of the QRS complex can indicate a change in a patient's cardiac health. For example, lengthening of the QRS complex can indicate progression of heart failure (HF) of the patient. The time frame of the change can also provide useful information. If the lengthening takes place over a matter of weeks, the change in duration may indicate a change in HF status. If the lengthening takes place within days, the change in duration may indicate a myocardial infarction (MI).

Patients with a wide QRS complex may be candidates to receive a CRT device. A CRT device reestablishes synchrony between contraction of the left ventricular free wall and ventricular septum. CRT may include bi-ventricular pacing or only left ventricular pacing.

Figure 3:
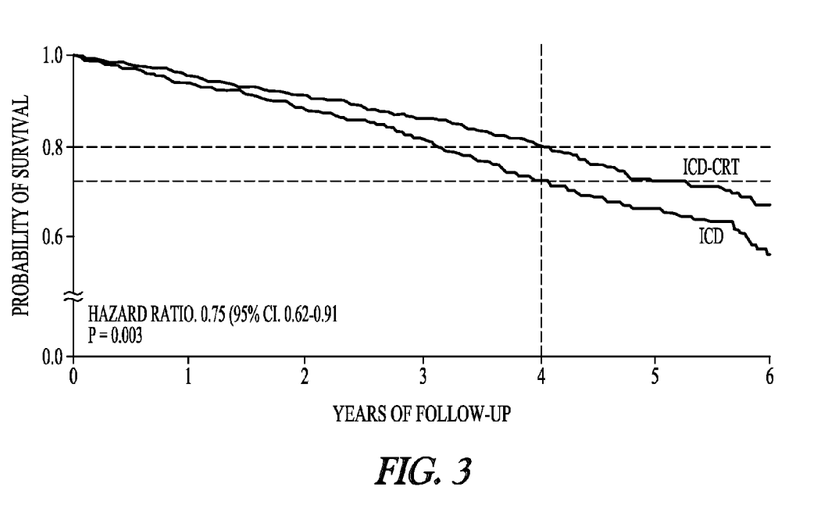
FIG. 3 is a graph showing the difference in the probability of survival of patients that receive an ICD and patients that receive an ICD with CRT capability.

FIG. 3 is a graph showing the difference in the probability of survival of patients that receive an ICD and patients that receive an ICD with CRT capability (ICD-CRT). The graph shows that at four years, there is a 45% increase in mortality in Class II/III patients when those patients have ICDs instead of ICD-CRTs. Monitoring the QRS complex may help identify those patients that would benefit from a CRT device. A problem in monitoring the duration of the QRS complex is the difficulty of implementing device recognition of the QRS complex.

Figure 4:
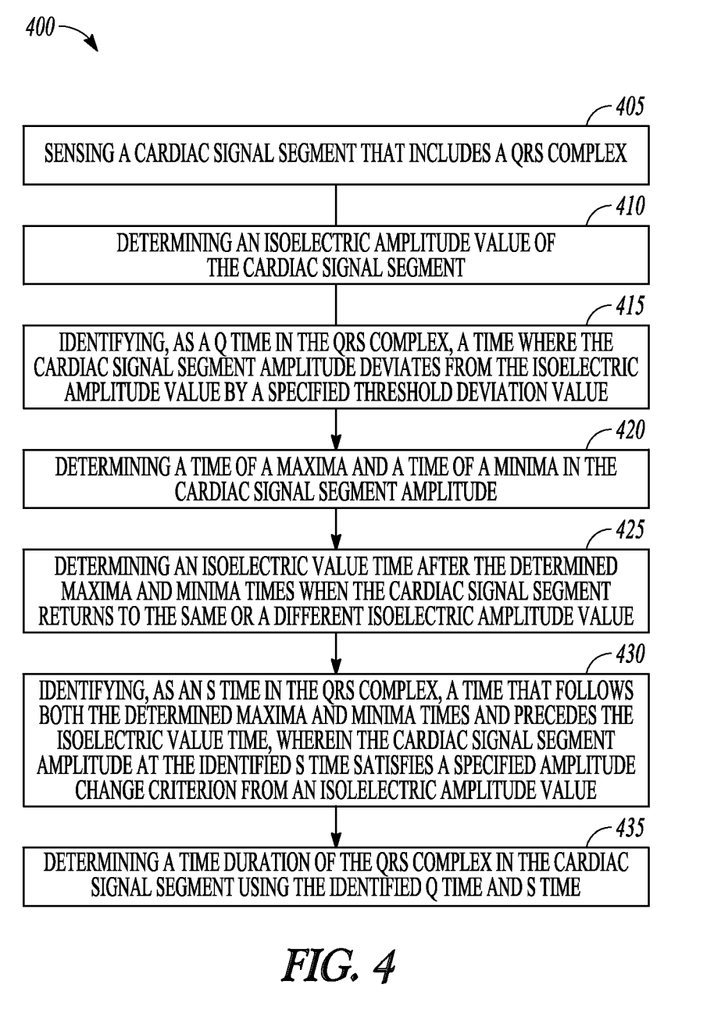
FIG. 4 is a flow diagram of an example of a method of monitoring the QRS complex with a medical device.

FIG. 4 is a flow diagram of an example of a method 400 of monitoring the QRS complex with a medical device. At block 405, a cardiac signal segment that includes a QRS complex is sensed. In some examples, the cardiac signal segment is a sensed ECG signal segment. In some examples, the cardiac signal segment is a sensed electrogram signal segment. At block 410, an isoelectric amplitude value of the cardiac signal segment is determined.

Figure 5:
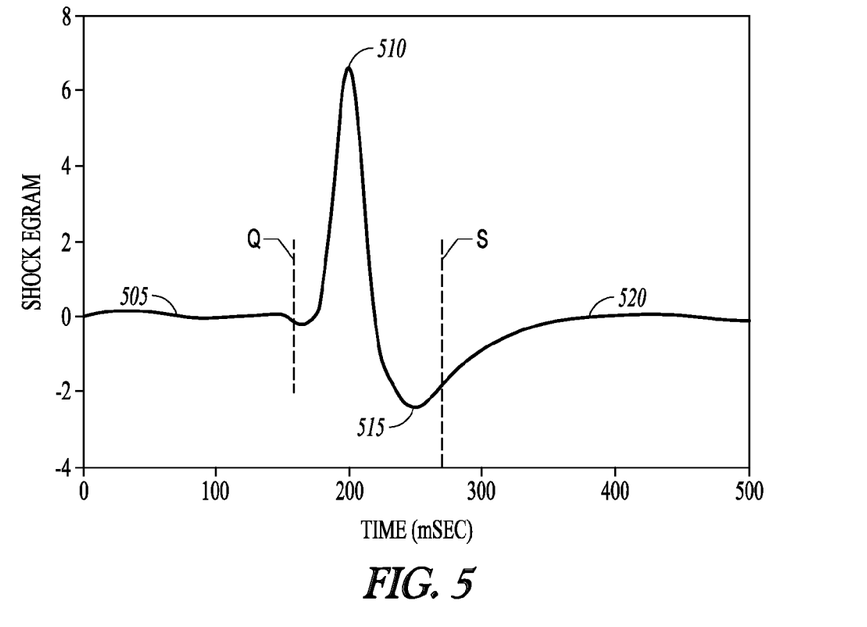
FIG. 5 illustrates an example of a cardiac signal segment that includes a QRS complex.

FIG. 5 illustrates an example of a cardiac signal segment that includes a QRS complex. In some examples, the isoelectric amplitude value can be zero volts as is shown in the Figure for segment portion 505. In some examples the isoelectric amplitude value can be the amplitude value for a portion of the cardiac signal segment that is maximally flat.

At block 415 of FIG. 4, a Q time in the QRS complex is identified. The Q time is identified as the time where the cardiac signal segment amplitude deviates from the isoelectric amplitude value by a specified threshold deviation value. The specified threshold deviation value can be specified as fixed value (e.g., a specified number of millivolts) or a specified fraction of a difference between the isoelectric amplitude value and the value of a maxima or minima in the cardiac signal segment. In FIG. 5, the Q time is approximately 160 milliseconds (ms).

At block 420, the time of a maxima and the time of a minima in the cardiac signal segment amplitude is determined. In FIG. 5, the time of the signal maxima 510 is about 200 ms and the time of the signal minima 515 is about 250 ms. At block 425, an isoelectric value time after the determined maxima and minima times is determined when the cardiac signal segment returns to the same or a different isoelectric amplitude value. In FIG. 5, the cardiac signal segment returns to the same isoelectric amplitude value of 0 volts after the signal maxima 510 and signal minima 515. The isoelectric value time 520 occurs at about 350 ms.

At block 430, an S time is identified in the QRS complex. The S time can be a time that follows both the determined maxima and minima times and precedes the isoelectric value time. The cardiac signal segment amplitude at the identified S time satisfies a specified amplitude change criterion from an isoelectric amplitude value. The time duration of the QRS complex in the cardiac signal segment is determined at block 435 using the identified Q time and S time.

In some examples, the S time can be identified as a fraction of the time from the minima or maxima to the isoelectric value time 520. The minima time can occur after the maxima time as in FIG. 5. In this case, the S time can be identified as a specified fraction of the time duration from the time of the minima to the isoelectric value time. In some examples, the maxima time follows the minima time (e.g., FIG. 5 inverted). In this case, the S time can be identified as a specified fraction of the time duration from the time of the maxima to the isoelectric value time.

Figure 6:
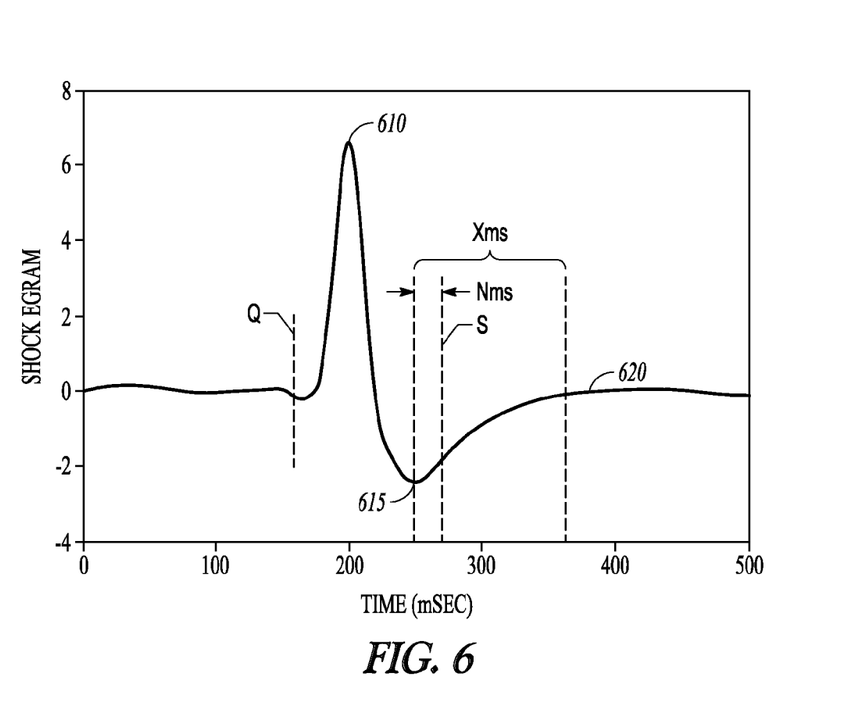
FIG. 6 shows an example of identifying the S time in a cardiac signal.

FIG. 6 shows an example of identifying the S time in a cardiac signal. The time of the minima 615 (about 250 ms) follows the time of the maxima 610 (about 200 ms). The duration of time from the minima 615 to the return to the isoelectric value time 620 is shown as X ms. The S time is chosen as a specified fraction of the time duration X ms and is denoted as N ms in the Figure. In certain examples, the specified fraction N can be a specified percentage of X. If X is 100 ms and N is 20%, then the S time is 20 ms after the minima time, or 270 ms. If the Q time is identified as 160 ms, the duration of the QRS complex is 110 ms (270 ms−160 ms).

In some examples, the S time can be identified as the time the cardiac signal segment returns to a specified fraction of the difference between the minima (or maxima) amplitude and the isoelectric amplitude value. When the minima time occurs after the maxima time, identifying the S time can include identifying a time that the amplitude of the cardiac signal segment is a specified fraction of the difference between the minima and the isoelectric amplitude value at the isoelectric value time. When the maxima time occurs after the minima time, identifying the S time can include identifying a time where the amplitude of the cardiac signal segment is a specified fraction of the difference between the maxima and the isoelectric amplitude value.

Figure 7:
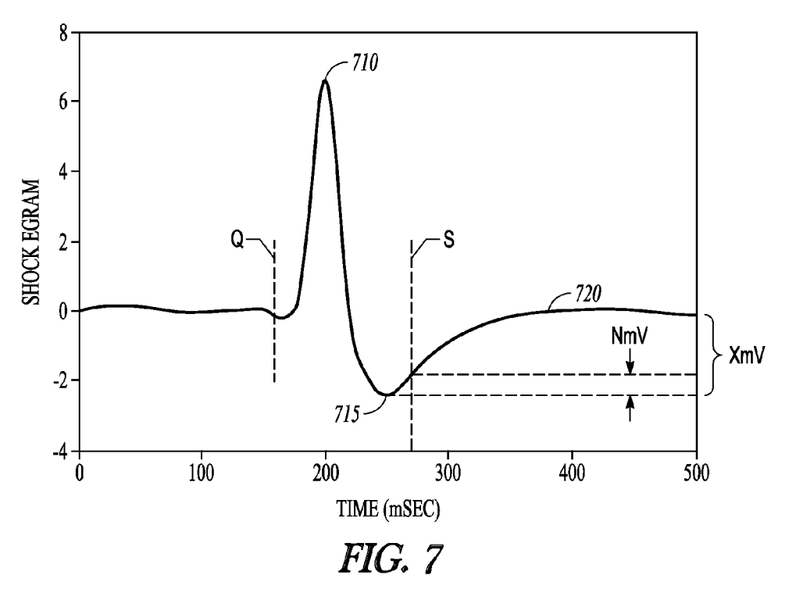
FIG. 7 shows another example of identifying the S time in a cardiac signal.

FIG. 7 shows another example of identifying the S time in a cardiac signal. The minima time 715 occurs after the maxima time 710. The difference between the amplitude at the minima time 715 and the isoelectric amplitude value is shown as X mV. A specified fraction of the amplitude difference is shown as N mV in the Figure. The S time is identified as the time in the cardiac signal when the signal increases N mV from the signal value at the minima 715.

In some examples, the S time can be identified by calculating a derivative of a portion of the cardiac signal segment that follows both the determined maxima and minima times and precedes the isoelectric value time. When the minima time occurs after the maxima time, the S time is identified as the time of a maximum of the derivative of the cardiac signal segment portion.

Figure 8:
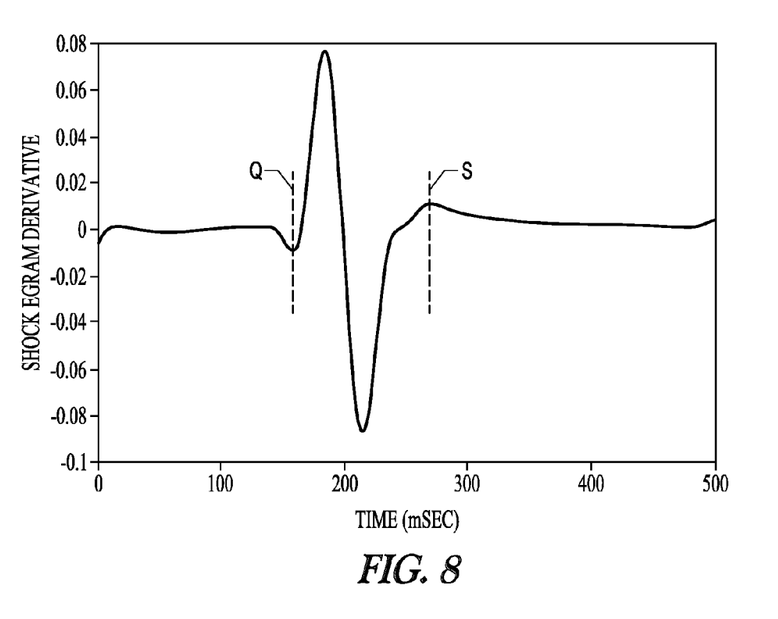
FIG. 8 shows an example of identifying the S time using a derivative of a sensed cardiac signal segment.

FIG. 8 shows an example of identifying the S time using a derivative of a sensed cardiac signal segment. FIG. 8 shows a waveform that represents the derivative of the waveform in FIG. 5. In FIG. 5, the minima time is about 250 ms. Therefore, the portion of the waveform of interest is after the 250 ms time in FIG. 8 to the isoelectric time. This portion can be viewed as the post R-wave recovery time. The Figure shows that the peak in this portion of the waveform is chosen as the S time. When the maxima time occurs after the minima time in the cardiac signal segment, the waveform in FIG. 5 would be inverted. In this case, the S time is identified as the time of a minimum of the derivative of the cardiac signal segment portion. The QRS duration is then calculated as the duration from the identified Q time to the identified S time (e.g., S time−Q time).

Figure 9:
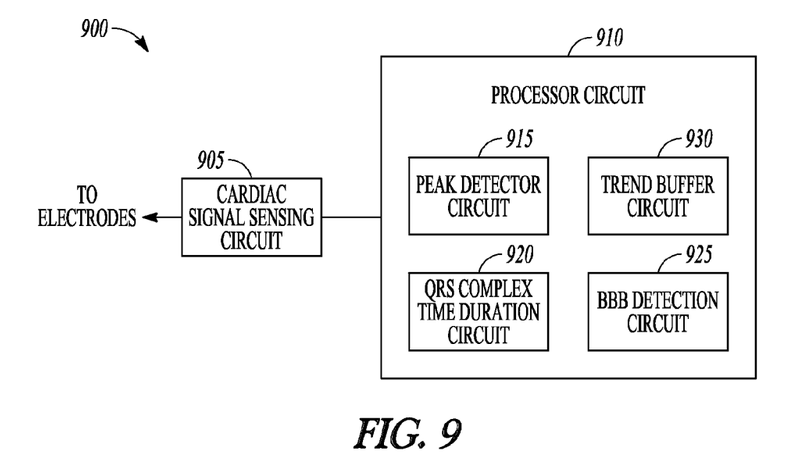
FIG. 9 is a block diagram of portions of an example of a medical device to monitor the duration of the QRS complex.

FIG. 9 is a block diagram of portions of an example of a medical device 900 to monitor the duration of the QRS complex. The device 900 includes a cardiac signal sensing circuit 905 and a processor circuit 910. The cardiac signal sensing circuit 905 senses a cardiac signal segment that includes a QRS complex. In some examples the device 900 is wearable and the cardiac signal sensing circuit 905 includes a surface (e.g., skin contact) ECG circuit to sense the cardiac signal.

In some examples the device 900 is implantable and the cardiac signal sensing circuit 905 includes implantable electrodes, a sense amplifier and a sampling circuit to sense an electrogram signal. In some examples, the cardiac signal sensing circuit 905 includes a unipolar sensing channel. Cardiac signal sensing circuits typically include a sensing electrode and a reference electrode. The terms bipolar sensing channel and unipolar sensing channel refer to how many electrodes are disposed in the vicinity of the heart. A bipolar sensing channel configuration has two electrodes that are in contact with the heart or are intracardiac. A unipolar configuration has a first electrode that is either in contact with the heart, is intracardiac, or is generally nearer the heart than the second electrode which is remote from the first electrode. Sensing the cardiac signal segment using a unipolar sensing channel may provide additional information regarding a ventricular depolarization as compared to using a bipolar sensing channel.

In some examples, the cardiac signal sensing circuit 905 is within an implantable housing, and the unipolar sensing channel includes a first electrode configured to provide at least one of cardioversion or defibrillation shock therapy (e.g., RV coil electrode 175 in FIG. 1) and a second electrode formed using the implantable housing. In some examples, the unipolar sensing channel includes a first electrode configured to sense a cardiac signal in a right ventricle (e.g., ring electrode 140 in FIG. 1) and a second electrode formed using the implantable housing.

In some examples, an implantable cardiac signal sensing circuit includes a wireless ECG circuit. A wireless ECG is a signal approximating the surface ECG and is acquired without using surface electrodes. An example of a circuit for sensing the wireless ECG is discussed in commonly assigned, co-pending U.S. Pat. No. 7,299,086, entitled "WIRELESS ECG IN IMPLANTABLE DEVICES," filed on Mar. 5, 2004, which is incorporated herein by reference in its entirety.

The processor circuit 910 is communicatively coupled to the cardiac signal sensing circuit 905. The communicative coupling allows the processor circuit 910 to receive electrical signals from the cardiac signal sensing circuit 905 even though there may be intervening circuitry. The processor circuit 910 can be an application specific integrated circuit (ASIC), a microprocessor, a digital signal processor, or other type of processor, interpreting or executing instructions in software modules or firmware modules. The processor circuit 910 can include other circuits or sub-circuits to perform the functions described. These circuits may include software, hardware, firmware or any combination thereof. Multiple functions can be performed in one or more of the circuits as desired.

In some examples, the cardiac signal sensing circuit 905 is implantable and the implantable cardiac signal sensing circuit and the processor circuit 910 are included in an implantable medical device. In some examples, the cardiac signal sensing circuit 905 is included in an implantable medical device and the processor circuit 910 is included in a second device (e.g., an external system or a remote external system).

The processor circuit 910 includes a peak detector circuit 915 and a QRS complex time duration circuit 920. The peak detector circuit 915 determines a time of a maxima and a time of a minima in the sensed cardiac signal segment. The QRS complex time duration circuit 920 identifies a Q time in the cardiac signal segment and an S time in the cardiac signal segment and determines the time duration of the QRS complex in the cardiac signal segment using the identified Q time and S time.

To identify the Q time, the QRS complex time duration circuit 920 determines an isoelectric amplitude value of the cardiac signal segment. In some examples, isoelectric amplitude values are determined from sampled values of the sensed cardiac signal segment. As explained previously, an isoelectric value of the signal can be defined to be zero volts or the amplitude of a maximally flat portion of the cardiac signal segment. The QRS complex time duration circuit 920 identifies, as a Q time in the QRS complex, a time where the cardiac signal segment amplitude deviates from the first isoelectric amplitude value by a specified threshold deviation value. An example of identifying the Q time or Q point was discussed previously in regard to FIG. 5.

To identify the S time, the QRS complex time duration circuit 920 determines an isoelectric value time after the determined maxima and minima times that the cardiac signal segment returns to the same or a different isoelectric amplitude value. The S time in the QRS complex is identified as the time that follows both the determined maxima and minima times and precedes the isoelectric value time. The cardiac signal segment amplitude at the identified S time satisfies a specified amplitude change criterion from an isoelectric amplitude value. The QRS complex time duration circuit 920 can be configured to identify the S time using any of the methods described previously in regard to FIGS. 5-8.

Figure 10:
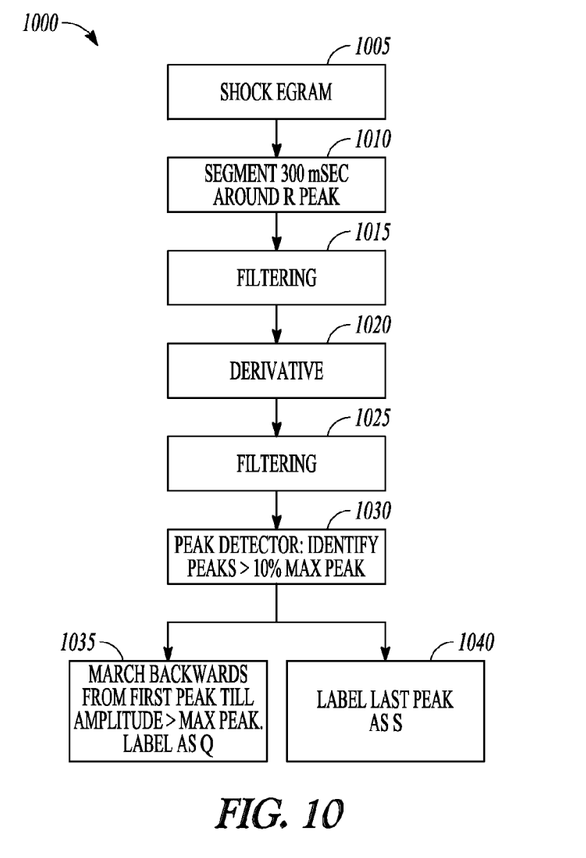
FIG. 10 shows another example of a method of determining the time duration of the QRS complex using a derivative of a sensed cardiac signal segment.

FIG. 10 shows an example of a method 1000 of determining the time duration of the QRS complex using a derivative of the sensed cardiac signal segment. The cardiac signal sensing circuit 905 includes electrodes included in a shock channel. At block 1005, an electrogram of a cardiac signal is sensed using the shock channel. In some examples, the cardiac signal sensing circuit 905 includes surface electrodes and a surface ECG is obtained.

At block 1010, the peak detector circuit 915 identifies the R-wave peak in the cardiac signal and a 300 ms segment around the R-wave peak is stored. At block 1015, the QRS complex time duration circuit 920 smoothes the cardiac signal segment. In some examples, the signal is smoothed using filtering. In certain examples, the filtering involves Savitzky-Golay filtering.

At block 1020, the QRS complex time duration circuit 920 calculates the derivative of the smoothed cardiac signal segment and, in certain examples, the derivative is smoothed at block 1025 (e.g., by filtering, such as Savitzky-Golay filtering).

At block 1030, the peak detector identifies peaks in the derivative signal that have amplitude more than ten percent of the R-wave peak amplitude. At block 1035, the QRS complex time duration circuit 920 marches backward (e.g., earlier) from the R-wave peak in the segment samples until a sample with signal amplitude greater than ten percent of the R-wave peak amplitude is detected. The time of this identified sample is labeled as the Q time.

At block 1040, the QRS complex time duration circuit 920 identifies the last peak in the 300 ms segment that has signal amplitude greater than ten percent of the R-wave peak amplitude. The time of this last peak is labeled as the S time. The QRS complex time duration is calculated as the difference between the Q-time and S time.

According to some examples, the detection of the Q time and S time can be refined by sensing the cardiac signal segment using multiple sensing channels or sensing vectors. For example, two cardiac signal segments could be sensed simultaneously using two unipolar sensing vectors, such as RV coil electrode 175 to can and ring electrode 140 to can for example. The Q time can be identified as the earliest Q time determined for these two vectors. In another example, two cardiac signal segments could be sensed simultaneously using a unipolar sensing vector and a bipolar sensing vector, such as RV coil electrode 175 to can and ring electrode 140 to tip electrode 135 for example. If the Q time determined from the bipolar sensing vector occurs earlier than the Q time determined from the unipolar sense vector, then the Q is determined as this earlier point from the bipolar sense vector.

In some examples, the QRS complex time duration circuit 920 is configured to calculate a confidence interval for the QRS complex time duration value. To calculate the confidence interval, QRS complex time durations calculated for N heart beats can be used, wherein N is a positive integer. In certain examples, the multiple QRS complex time durations can be taken using multiple sensing vectors. The QRS complex time duration circuit 920 may then determine the sample mean (u) and standard deviation (sigma) of these measurements. The confidence interval CI can be determined as $$CI=[u-k*sigma, u+k*sigma],$$

where k is a variable dependent on the desired confidence level (e.g. for 95% confidence, k=1.96, assuming QRS width thus measured follows a normal distribution). In some examples, the QRS complex time duration circuit 920 provides the determined QRS complex time duration value and confidence interval value to at least one of a user or process. In some examples, an alert is generated or a level of alert is increased when the calculated interval for a desired confidence exceeds a specified threshold.

In some examples, measurements of the time duration of the QRS complex are trended. The processor circuit 910 can include a trend buffer circuit 930 integral to or communicatively coupled to the processor circuit 910 and configured to store determined time durations for QRS complexes. This can be useful to detect changes in a patient's QRS complex time duration that may have resulted from events such as hospitalization or delivery of anti-tachycardia therapy.

The processor circuit 910 trends the QRS time duration using stored time duration values. The trend buffer circuit 930 stores the most M recent calculated QRS complex time durations, where M is a positive integer (e.g., M=60). In some examples, the trend buffer is updated so that the last buffer entry is the most recent and the first entry in the buffer is the mean value (u) of the time durations plus one standard deviation (sigma), or the last buffer entry=u+sigma.

If an alert condition is detected by the trending, the processor circuit 910 may change the size of the trend buffer (e.g., M is changed from 60 to 120 storage locations) to collect additional information. In some examples, the processor circuit 910 changes the amount of storage in the trend buffer circuit 930 in response to detecting at least one of an expected value of the width of the QRS complex determined from the trending or a deviation of the width in the QRS complex from an expected trend value of the width.

According to some examples, the medical device 900 is able to detect bundle branch block (BBB). In certain examples, the medical device is able to discern or discriminate left bundle branch block (LBBB) from right bundle branch block (RBBB).

Figure 11:
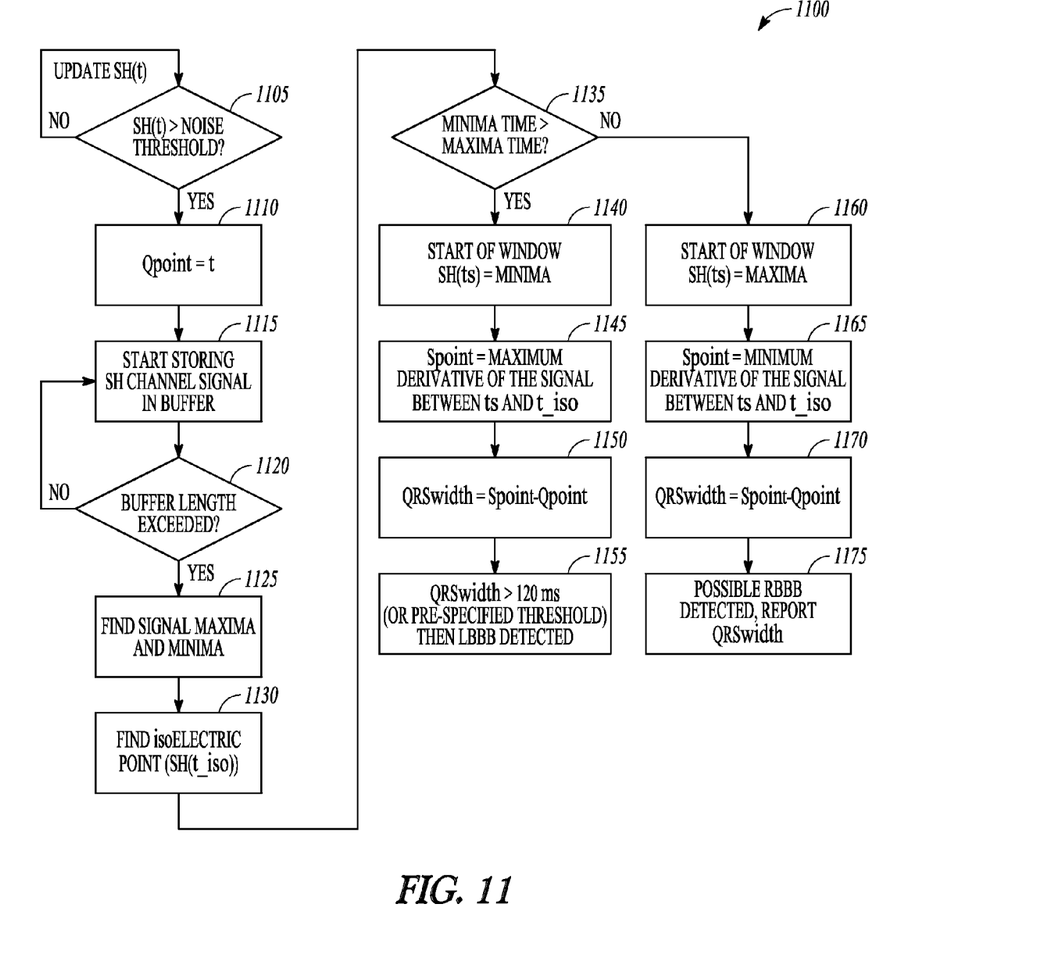
FIG. 11 shows an example of a method of determining the QRS width or time duration, and of detecting bundle branch block.

FIG. 11 shows an example of a method 1100 of determining the QRS width or time duration and detecting BBB. In some examples, the cardiac signal is sensed using a shock channel and the sensed cardiac signal is sampled. At block 1105, it is determined whether the sampled signal at time t (SH(t)), is above a noise threshold. If the samples are above the noise threshold, the Q point (or Q time) is determined at block 1110, such as by detecting a point where the cardiac signal segment amplitude deviates from an isoelectric amplitude value by a specified threshold deviation value for example. The sampled signal is stored in a buffer at block 1115 until a buffer size criterion is satisfied at block 1120.

At block 1125 the maxima and the minima are found in the stored cardiac signal segment. At block 1130, the isoelectric point after the minima and maxima (SH(t_iso)) is found. At block 1135, it is determined if the minima time occurs after maxima time.

If the minima occurs after the maxima, at block 1140 a segment window is established that begins at the time of the minima (e.g., start time SH(ts)=minima time) and ends at the time of the isoelectric point (SH(t_iso)). At block 1145, the derivative over the segment window (from SH(ts) to SH(t_iso)) is determined and the S point is identified as the time of the maximum amplitude in the derivative.

At block 1150, the QRS width is determined as the difference between the S point and the Q point. At block 1155, if the QRS width exceeds a pre-specified threshold (e.g., 120 ms), then LBBB is declared detected.

At block 1160, if the maxima occurs after the minima, a segment window is established that begins at the time of the maxima (e.g., start time SH(ts)=maxima time) and ends at the time of the isoelectric point (SH(t_iso)). At block 1165, the derivative over the segment window (from SH(ts) to SH(t_iso)) is determined and the S point is identified as the time of the minimum amplitude in the derivative.

At block 1170, the QRS width is determined as the difference between the S point and the Q point. At block 1175, possible RBBB is reported because the maxima followed the minima. In some examples, the QRS width is provided with the indication of possible RBBB.

Returning to FIG. 9, to detect BBB the processor circuit 910 includes a bundle branch block (BBB) detection circuit 925. The BBB detection circuit generates an indication of left bundle branch block (LBBB) when the minima time occurs after the maxima time and the time duration of the QRS complex exceeds a specified threshold time duration value, and provides the indication of LBBB to at least one of a user or process. The BBB detection circuit 925 may also generate an indication of possible right bundle branch block (RBBB) when the maxima time occurs after the minima time and provide the indication to at least one of a user or process.

In some examples, BBB detection circuit 925 generates an indication of at least one of RBBB or LBBB according to the time relationship of the determined maxima and minima times, the determined QRS complex time duration, and the calculated confidence interval for the QRS complex time duration.

Identifying patients that have wide QRS complexes can lead to improved therapy for the patients, such as by implanting the patients with a medical device can deliver cardiac resynchronization therapy. Early identification of patients who have wide QRS complexes may improve mortality of patient with cardiac disease.

Additional Notes

Example 1 includes Subject matter (such as a system) comprising a cardiac signal sensing circuit configured to sense a cardiac signal segment that includes a QRS complex and a processor circuit communicatively coupled to the cardiac signal sensing circuit. The processor circuit includes a peak detector circuit configured to determine a time of a maxima and a time of a minima in the cardiac signal segment, and a QRS complex time duration circuit. The QRS complex time duration circuit is configured to determine an isoelectric amplitude value of the cardiac signal segment, identify, as a Q time in the QRS complex, a time where the cardiac signal segment amplitude deviates from the first isoelectric amplitude value by a specified threshold deviation value, determine an isoelectric value time after the determined maxima and minima times that the cardiac signal segment returns to the same or a different isoelectric amplitude value, identify, as an S time in the QRS complex, a time that follows both the determined maxima and minima times and precedes the isoelectric value time, wherein the cardiac signal segment amplitude at the identified S time satisfies a specified amplitude change criterion from an isoelectric amplitude value, and determine a time duration of the QRS complex in the cardiac signal segment using the identified Q time and S time.

In Example 2, the subject matter of Example 1 can optionally include a QRS complex time duration circuit that can be configured to calculate a derivative of the portion of the cardiac signal segment that follows both the determined maxima and minima times and precedes the isoelectric value time, identify as the S time, when the minima time occurs after the maxima time, a time of a maximum of the derivative of the cardiac signal segment portion, and identify as the S time, when the maxima time occurs after the minima time, a time of a minimum of the derivative of the cardiac signal segment portion.

In Example 3, the subject matter of one or any combination of Examples 1 and 2 can optionally include a QRS complex time duration circuit that can be configured to identify as the S time, when the minima time occurs after the maxima time, a time that the amplitude of the cardiac signal is a specified fraction of the difference between the minima and the isoelectric amplitude value at the isoelectric value time, and identify as the S time, when the maxima time occurs after the minima time, a time where the amplitude of the cardiac signal is a specified fraction of the difference between the maxima and the isoelectric amplitude value.

In Example 4, the subject matter of one or any combination of Examples 1-3 can optionally include a QRS complex time duration circuit that can be configured to identify as the S time, when the minima time occurs after the maxima time, a specified fraction of the time duration from the time of the minima to the isoelectric value time, and identify as the S time, when the maxima time occurs after the minima time, a specified fraction of the time duration from the time of the maxima to the isoelectric value time.

In Example 5, the subject matter of one or any combination of Examples 1-4 can optionally include an implantable cardiac signal sensing circuit that can include a unipolar sensing channel.

In Example 6, the subject matter of one or any combination of Examples 1-5 can optionally include a cardiac signal sensing circuit within an implantable housing, and a unipolar sensing channel that can include a first electrode configured to provide at least one of cardioversion or defibrillation shock therapy and a second electrode formed using the implantable housing.

In Example 7, the subject matter of one or any combination of Examples 1-5 can optionally include a cardiac signal sensing circuit within an implantable housing, and a unipolar sensing channel that includes a first electrode configured to sense a cardiac signal in a right ventricle and a second electrode formed using the implantable housing.

In Example 8, the subject matter of one or any combination Examples 1-7 can optionally include a processor circuit that can include a bundle branch block (BBB) detection circuit configured to generate an indication of left bundle branch block (LBBB) when the minima time occurs after the maxima time and the time duration of the QRS complex exceeds a specified threshold time duration value, and provide the indication of LBBB to at least one of a user or process.

In Example 9, the subject matter of one or any combination Examples 1-8 can optionally include a processor circuit that can include a BBB detection circuit configured to generate an indication of possible right bundle branch block (RBBB) when the maxima time occurs after the minima time, and provide the indication to at least one of a user or process.

In Example 10, the subject matter of one or any combination of Examples 1-9 can optionally include a QRS complex time duration circuit that can be configured to calculate a confidence interval for the QRS complex time duration value using QRS complex time durations calculated for N heart beats, wherein N is a positive integer, and provide the determined QRS complex time duration value and confidence interval value to at least one of a user or process.

In Example 11, the subject matter of one or any combination Examples 1-10 can optionally include a BBB detection circuit configured to generate an indication of at least one of RBBB or LBBB according to the time relationship of the determined maxima and minima times, the determined QRS complex time duration, and the calculated confidence interval for the QRS complex time duration.

In Example 12, the subject matter of claim 11 can optionally include a trend buffer circuit integral to or communicatively coupled to the processor circuit and configured to store determined time durations for QRS complexes; and the processor circuit can be configured to trend the time duration using stored time duration values and to change an amount of storage in the trend buffer circuit in response to detecting at least one of an expected value of the width of the QRS complex determined from the trending, and a deviation of the width in the QRS complex from an expected trend value of the width.

In Example 13, the subject matter of one or any combination of Examples 1-12 can optionally include an implantable cardiac signal sensing circuit and the processor circuit can be included in an implantable medical device.

In Example 14, the subject matter of one or any combination of Examples 1-12 can optionally include an implantable medical device and the processor circuit can be included in a second device.

Example 15 can include subject matter, or can optionally be combined with the subject matter of one or any combination of Examples 1-14 to include subject matter (such as a method, a means for performing acts, or a machine-readable medium including instructions that, when performed by the machine, cause the machine to perform acts) comprising sensing a cardiac signal segment that includes a QRS complex, determining an isoelectric amplitude value of the cardiac signal segment, identifying, as a Q time in the QRS complex, a time where the cardiac signal segment amplitude deviates from the isoelectric amplitude value by a specified threshold deviation value, determining a time of a maxima and a time of a minima in the cardiac signal segment amplitude, determining an isoelectric value time after the determined maxima and minima times that the cardiac signal segment returns to the same or a different isoelectric amplitude value, identifying, as an S time in the QRS complex, a time that follows both the determined maxima and minima times and precedes the isoelectric value time, wherein the cardiac signal segment amplitude at the identified S time satisfies a specified amplitude change criterion from an isoelectric amplitude value, and determining a time duration of the QRS complex in the cardiac signal segment using the identified Q time and S time.

Such subject matter can include means for sensing a cardiac signal segment that includes a QRS complex, illustrative examples of which can include a surface ECG circuit, an implantable electrodes, a sense amplifier and a sampling circuit, a unipolar sensing channel, bipolar sensing channel, an electrode formed on an implantable housing, an electrode configured to provide at least one of cardioversion or defibrillation shock therapy, an electrode configured to sense a cardiac signal in a right ventricle, and a wireless ECG circuit.

Such subject matter can include means for determining an isoelectric amplitude value of the cardiac signal segment, an illustrative example of which include a processor circuit having a QRS complex time duration circuit. Illustrative examples of a processor circuit include a microprocessor, a digital signal processor, ASIC, or other type of processor, interpreting or executing instructions in software modules or firmware modules.

Such subject matter can include means for identifying, as a Q time in the QRS complex, a time where the cardiac signal segment amplitude deviates from the isoelectric amplitude value by a specified threshold deviation value, an illustrative example of which includes a processor circuit having a QRS complex time duration circuit.

Such subject matter can include means for determining a time of a maxima and a time of a minima in the cardiac signal segment amplitude, an illustrative example of which includes a peak detector circuit.

Such subject matter can include means for determining an isoelectric value time after the determined maxima and minima times that the cardiac signal segment returns to the same or a different isoelectric amplitude value, an illustrative example of which includes a processor circuit having a QRS complex time duration circuit.

Such subject matter can include a means for identifying, as an S time in the QRS complex, a time that follows both the determined maxima and minima times and precedes the isoelectric value time, an illustrative example of which includes a processor circuit having a QRS complex time duration circuit.

Such subject matter can include means for determining a time duration of the QRS complex in the cardiac signal segment using the identified Q time and S time, an illustrative example of which includes a processor circuit having a QRS complex time duration circuit.

In Example 16, the subject matter of Example 15 can optionally include identifying the S time, which can include calculating a derivative of a portion of the cardiac signal segment that follows both the determined maxima and minima times and precedes the isoelectric value time, identifying as the S time, when the minima time occurs after the maxima time, a time of a maximum of the derivative of the cardiac signal segment portion, and identifying as the S time, when the maxima time occurs after the minima time, a time of a minimum of the derivative of the cardiac signal segment.

In Example 17, the subject matter of Example 15 can optionally include identifying, as the S time, when the minima time occurs after the maxima time, a time that the amplitude of the cardiac signal segment is a specified fraction of the difference between the minima and the isoelectric amplitude value at the isoelectric value time; and identifying as the S time, when the maxima time occurs after the minima time, a time where the amplitude of the cardiac signal segment is a specified fraction of the difference between the maxima and the isoelectric amplitude value.

In Example 18, the subject matter of one or any combination of Examples 15 and 17 can optionally include identifying as the S time, when the minima time occurs after the maxima time, a specified fraction of the time duration from the time of the minima to the isoelectric value time, and identifying as the S time, when the maxima time occurs after the minima time, a specified fraction of the time duration from the time of the maxima to the isoelectric value time.

In Example 19, the subject matter of one or any combination of Examples 15-19 can optionally include generating an indication of LBBB when the minima time occurs after the maxima time and the time duration of the QRS complex exceeds a specified threshold time duration value, generating an indication of possible RBBB when the maxima time occurs after the minima time, and providing a generated indication to at least one of a user or process.

In Example 20, the subject matter of one or any combination of Examples 15-20 can optionally include calculating a confidence interval for the QRS complex time duration value using QRS complex time durations calculated for N heart beats, wherein N is a positive integer, and providing an indication of bundle branch block (BBB) according to the determined QRS complex time duration value, wherein the indication includes the determined QRS complex time duration value and the confidence interval.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." In the event of inconsistent usages between this document and documents incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   a cardiac signal sensing circuit configured to sense a cardiac signal segment when operatively coupled to electrodes that contact a patient, wherein the cardiac signal segment includes a QRS complex;
   a processor circuit communicatively coupled to the cardiac signal sensing circuit, wherein the processor circuit includes:
   a peak detector circuit configured to determine a time of a maxima and a time of a minima in the sensed cardiac signal segment; and
   a QRS complex time duration circuit configured to:
      determine an isoelectric amplitude value of the cardiac signal segment;
      identify, as a Q time in the QRS complex, a time where the amplitude of the sensed cardiac signal segment deviates from the first isoelectric amplitude value by a specified amplitude threshold value;
      determine an isoelectric value time after the determined maxima and minima times that the cardiac signal segment returns to the same or a different isoelectric amplitude value;
      identify, as an S time in the QRS complex, a time that follows both the determined maxima and minima times and precedes the isoelectric value time, wherein the amplitude of the sensed cardiac signal segment at the identified S time satisfies a specified amplitude change criterion from the isoelectric amplitude value, and wherein the amplitude change criterion is chosen according to a determined relation of the maxima time to the minima time; and
      generate a value of a time duration of the QRS complex in the cardiac signal segment using the identified Q time and S time.

2. The system of claim 1, wherein the QRS complex time duration circuit is configured to:
   calculate a derivative of the portion of the cardiac signal segment that follows both the determined maxima and minima times and precedes the isoelectric value time;
   identify as the S time, when the minima time occurs after the maxima time, a time of a maximum of the derivative of the cardiac signal segment portion; and
   identify as the S time, when the maxima time occurs after the minima time, a time of a minimum of the derivative of the cardiac signal segment portion.

3. The system of claim 1, wherein the QRS complex time duration circuit is configured to:
   identify as the S time, when the minima time occurs after the maxima time, a time that the amplitude of the cardiac signal is a specified fraction of the difference between the minima and the isoelectric amplitude value at the isoelectric value time; and
   identify as the S time, when the maxima time occurs after the minima time, a time where the amplitude of the cardiac signal is a specified fraction of the difference between the maxima and the isoelectric amplitude value.

4. The system of claim 1, wherein the QRS complex time duration circuit is configured to:
   identify as the S time, when the minima time occurs after the maxima time, a specified fraction of the time duration from the time of the minima to the isoelectric value time; and
   identify as the S time, when the maxima time occurs after the minima time, a specified fraction of the time duration from the time of the maxima to the isoelectric value time.

5. The system of claim 1, wherein the cardiac signal sensing circuit is implantable and includes a unipolar sensing channel.

6. The system of claim 5, wherein the cardiac signal sensing circuit is within an implantable housing, and wherein the unipolar sensing channel includes a first electrode configured to provide at least one of cardioversion or defibrillation shock therapy and a second electrode formed using the implantable housing.

7. The system of claim 5, wherein the cardiac signal sensing circuit is within an implantable housing, and wherein the unipolar sensing channel includes a first electrode configured to sense a cardiac signal in a right ventricle and a second electrode formed using the implantable housing.

8. The system of claim 1, wherein the processor circuit includes a bundle branch block (BBB) detection circuit configured to:
   generate an indication of left bundle branch block (LBBB) when the minima time occurs after the maxima time and the time duration of the QRS complex exceeds a specified threshold time duration value; and
   provide the indication of LBBB to at least one of a user or process.

9. The system of claim 1, wherein the processor circuit includes a BBB detection circuit configured to:
   generate an indication of possible right bundle branch block (RBBB) when the maxima time occurs after the minima time; and
   provide the indication to at least one of a user or process.

10. The system of claim 1, wherein the QRS complex time duration circuit is configured to:

calculate a confidence interval for the QRS complex time duration value using QRS complex time durations calculated for N heart beats, wherein N is a positive integer; and provide the determined QRS complex time duration value and confidence interval value to at least one of a user or process.

11. The system of claim 10, wherein the processor circuit includes a BBB detection circuit configured to generate an indication of at least one of RBBB or LBBB according to the time relationship of the determined maxima and minima times, the determined QRS complex time duration, and the calculated confidence interval for the QRS complex time duration.

12. The system of claim 1, including:
a trend buffer circuit integral to or communicatively coupled to the processor circuit and configured to store determined time durations for QRS complexes; and
wherein the processor circuit is configured to trend the time duration using stored time duration values and to change an amount of storage in the trend buffer circuit in response to detecting at least one of:
an expected value of the width of the QRS complex determined from the trending; and
a deviation of the width e QRS complex from an expected trend value of the width.

13. The system of claim 1, wherein the implantable cardiac signal sensing circuit and the processor circuit are included in an implantable medical device.

14. The system of claim 1, wherein the implantable cardiac signal sensing circuit is included in an implantable medical device and the processor circuit is included in a second device.

15. An ambulatory medical device comprising:
a cardiac signal sensing circuit configured to sense a cardiac signal segment when operatively coupled to electrodes that contact a patient, wherein the cardiac signal segment includes a QRS complex;
a peak detector circuit configured to determine a time of a maxima and a time of a minima in the cardiac signal segment; and
a QRS complex time duration circuit is configured to:
determine a time of return to an isoelectric amplitude value after the determined maxima and minima times of the cardiac signal segment;
generate a value of an S time of the QRS complex as a time, following the determined maxima and minima times and preceding the time of return to the isoelectric amplitude value, at which the amplitude of the sensed cardiac signal segment satisfies a specified amplitude change criterion from the isoelectric amplitude value, and wherein the amplitude change criterion is chosen according to a determined relation of the maxima time to the minima time; and
calculate and store a value of time duration of the QRS complex using the generated value of the S time.

16. The ambulatory medical device of claim 15, wherein the QRS complex time duration circuit is configured to generate an indication of a type of bundle breach block (BBB) using the calculated time duration of the QRS complex and the determined relation of the maxima time to the minima time; and provide the indication to a user or process.

17. The ambulatory medical device of claim 15, wherein the QRS complex time duration circuit is configured to:
calculate a derivative of amplitude of the portion of the sensed cardiac signal segment that follows both the determined maxima and minima times and precedes the isoelectric value time;
identify a time of maximum amplitude in the derivative of the sensed cardiac signal segment portion as the S time when determining the minima time occurs after the maxima time; and
identify a time of minimum amplitude in the derivative of the sensed cardiac signal segment portion as the S time when determining the maxima time occurs after the minima time.

18. The ambulatory medical device of claim 15, wherein the QRS complex time duration circuit is configured to:
identify as the S time, a time that the amplitude of the sensed cardiac signal satisfies an amplitude change threshold specified as a fraction of the difference between the minima and the isoelectric amplitude value at the isoelectric value time when determining the minima time occurs after the maxima time; and
identify as the S time, a time that the amplitude of the sensed cardiac signal satisfies an amplitude change threshold specified as a fraction of the difference between the maxima and the isoelectric amplitude value at the isoelectric value time when determining the maxima time occurs after the minima time.

19. The ambulatory medical device of claim 15, wherein the QRS complex time duration circuit is configured to:
identify as the S time a specified fraction of the time duration from the time of the minima to the isoelectric value time when the minima time occurs after the maxima time; and
identify as the S time a specified fraction of the time duration from the time of the maxima to the isoelectric value time when the maxima time occurs after the minima time.

20. The ambulatory medical device of claim 15, wherein the QRS complex time duration circuit is configured to:
determine a first isoelectric value time prior to the determined maxima and minima times that the sensed cardiac signal segment has an isoelectric amplitude value;
generate a value of a Q time of the QRS complex as a time, preceding the determined maxima and minima times and following the first isoelectric value time, at which a change in amplitude of the sensed cardiac signal segment differs from the first isoelectric amplitude time value by a specified Q time amplitude change threshold;
generate the value of the S time as a time at which a change in amplitude of the sensed cardiac signal segment differs from the isoelectiic amplitude return value by a specified S time amplitude change threshold.

* * * * *